United States Patent [19]

Koths et al.

[11] Patent Number: 4,568,645

[45] Date of Patent: Feb. 4, 1986

[54] FUNGAL PYRANOSE-2-OXIDASE PREPARATIONS

[75] Inventors: Kirston E. Koths, Berkeley; Robert F. Halenbeck, San Rafael; David B. Ring, Redwood City, all of Calif.

[73] Assignee: Cetus Corporation, Emeryville, Calif.

[21] Appl. No.: 583,152

[22] Filed: Feb. 24, 1984

[51] Int. Cl.[4] .................... C12N 9/04; C12R 1/645
[52] U.S. Cl. .................................. 435/190; 435/911
[58] Field of Search ........................................ 435/190

[56] References Cited

U.S. PATENT DOCUMENTS

| | | | |
|---|---|---|---|
| 4,246,347 | 1/1981 | Neidleman et al. | 435/105 |
| 4,321,323 | 3/1982 | Maselli et al. | 435/105 |
| 4,321,324 | 3/1982 | Maselli et al. | 435/105 |
| 4,351,902 | 9/1982 | Neidleman et al. | 435/137 |
| 4,423,149 | 12/1983 | Amon et al. | 435/105 |
| 4,440,855 | 4/1984 | Horwath et al. | 435/105 |
| 4,442,207 | 4/1984 | Horwath et al. | 435/105 |

OTHER PUBLICATIONS

Jansen et al., "Pyranose Oxidase from *Polyporous obtusus*" in Methods in Enzymology, vol. 41, pp. 170–173 (1975).
T. E. Liu et al., Convenient Laboratory Procedure for Producing Solid D-*arabino*-Hexos-2-ulose (D-Glucosone), Carbohydrate Research 113, 151–157 (1983).
J. Volc et al., Conversion of Monosaccharides into Their Corresponding 2-Glycosuloses by Intact Cells of the Basidiomycete *Oudemansiella mucida*, Coll. Czech. Chem. Comm., 45, 950–955 (1980).
R. Baute et al., Cortalcerone, a New Antibiotic Induced by External Agents in *Corticium Caeruleum*, Phytochemistry, 15, 1753–1755 (1976).
R. Baute et al., Conversion of Glucose to Cortalcerone via Glucosone by *Corticium Caeruleum*, Phytochemistry 16, 1895–1897 (1977).
H. Ruelius et al., Carbohydrate Oxidase, a Novel Enzyme from *Polyporus obtusus* I. Isolation and Purification, Biochim Biophys. Acta, 167, 493–500 (1968).
F. Janssen and H. Ruelius, Carbohydrate Oxidase, a Novel Enzyme from *Polyporus obtusus* II. Specificity and Characterization of Reaction Products, Biochim et Biophys. Acta, 167, 501–510 (1968).
K. Uehara and M. Horiguchi, Enzymic Studies of *D. arabino*-Hexosulose IV. Autooxidation of *D-arabino-* Hexosulose, Chem. Abstracts, vol. 76, No. 14827f.
C. Robertson Bond et al., The Production of Glucosone from Carbohydrates by Enzymic Action, Biochemical J., 31, 1033–1040 (1937).
C. Berkeley, The Oxidase and Dehydrogenase Systems of the Crystalline Style of Mollusca, Biochemical J., 27, 1357–1365 (1933).
T. Kennedy Walker, A Biological Conversion of Glucose to Glucosone, Nature, 130, 582 (1932).

Primary Examiner—Lionel M. Shapiro
Attorney, Agent, or Firm—Albert P. Halluin; Elliott L. Fineman; Thomas E. Ciotti

[57] ABSTRACT

A substantially pure pyranose-2-oxidase preparation obtained from *C. versicolor* or *L. betulinus*. The preparation is substantially free of glucosone-utilizing enzyme contaminants having measurable activity at a pH between about 4.4 and 7.0.

6 Claims, 9 Drawing Figures

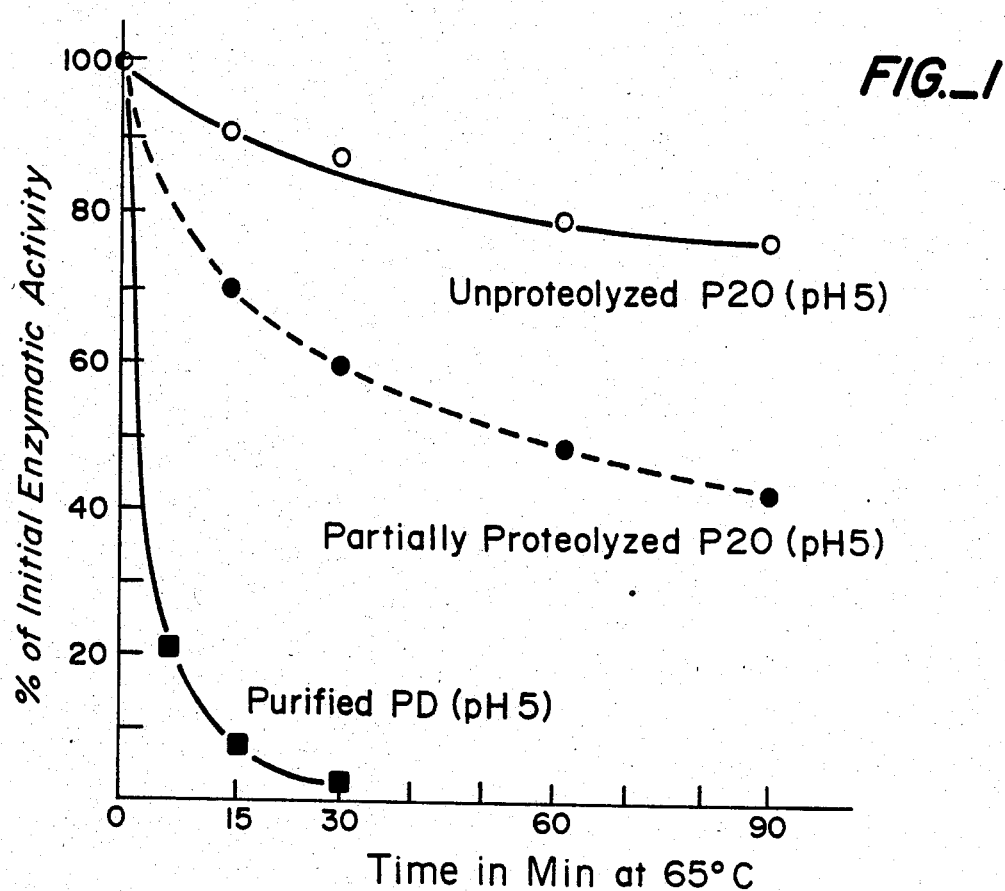
FIG._1
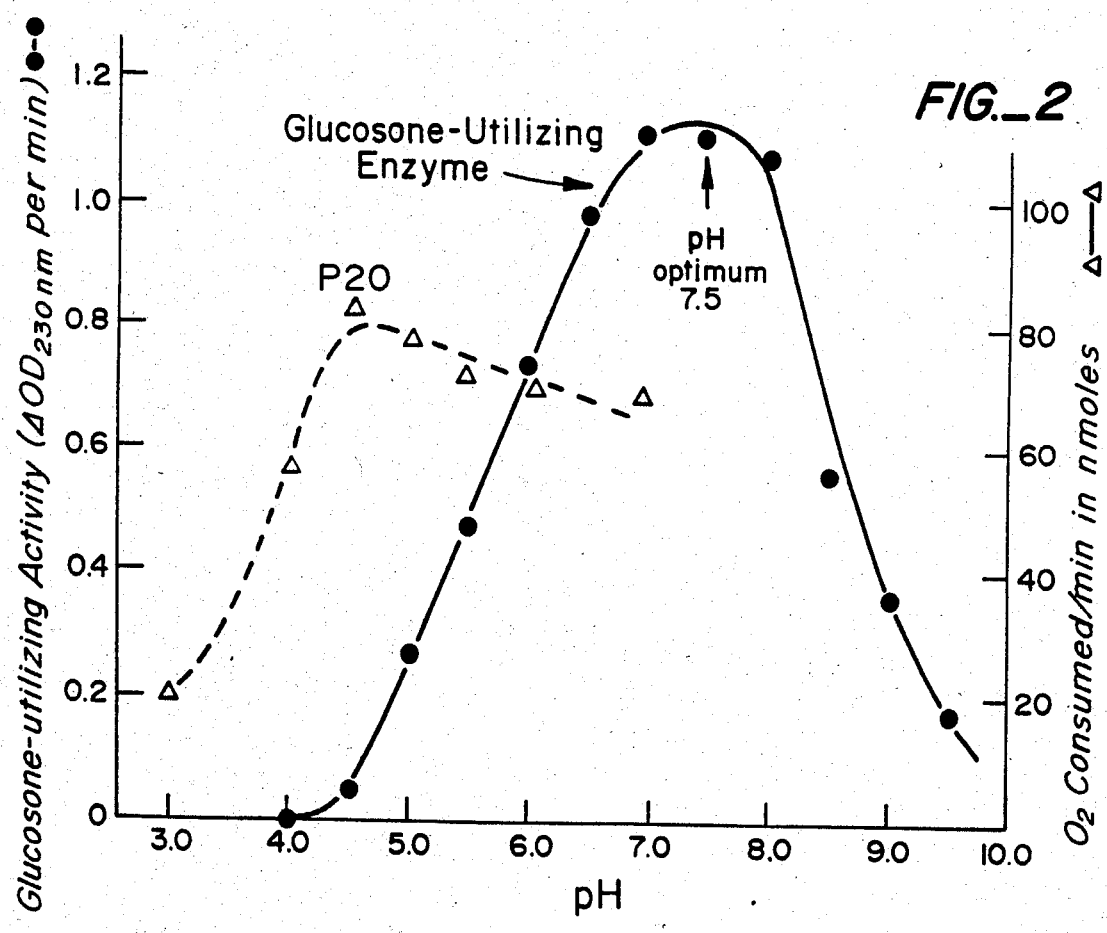
FIG._2

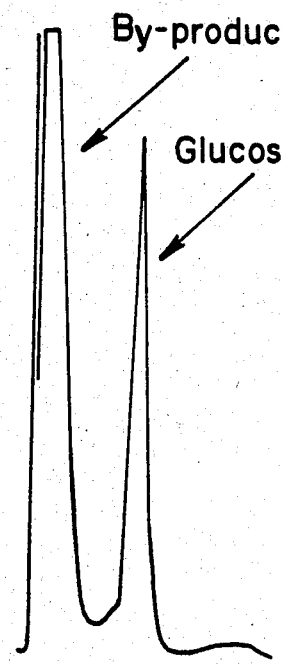
FIG._3A
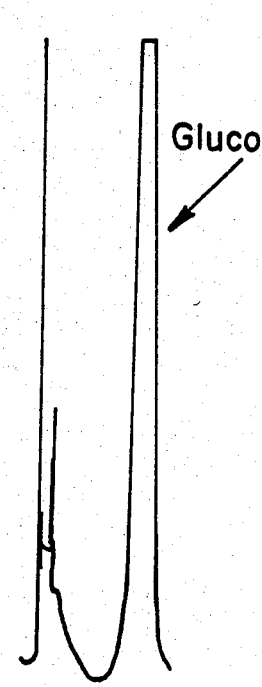
FIG._3B
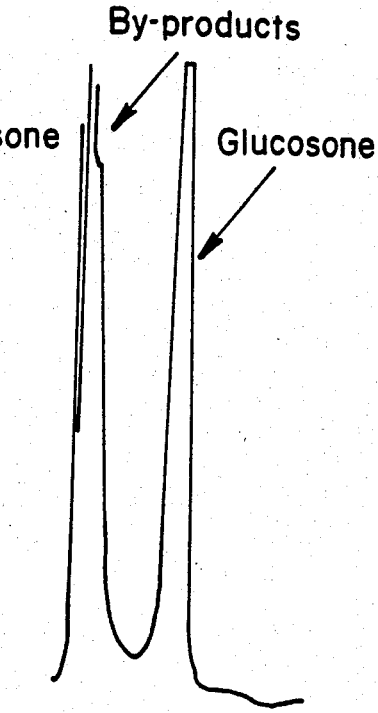
FIG._3C
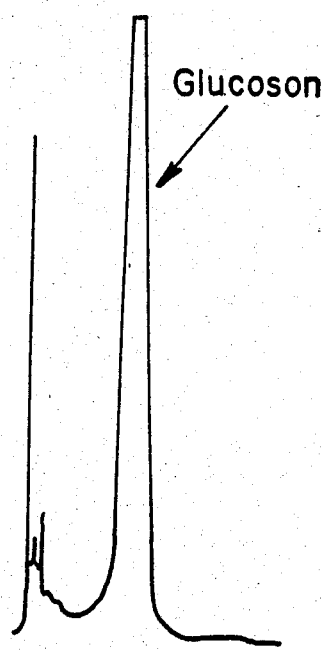
FIG._3D
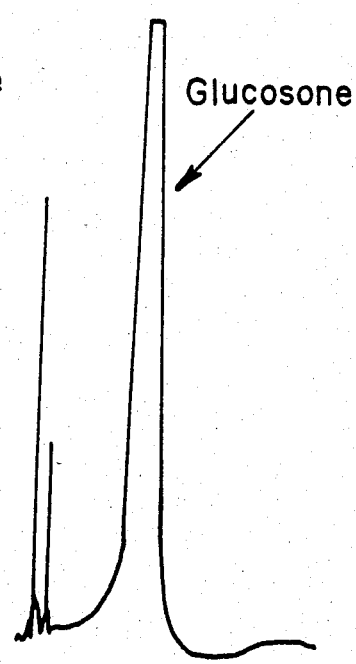
FIG._3E

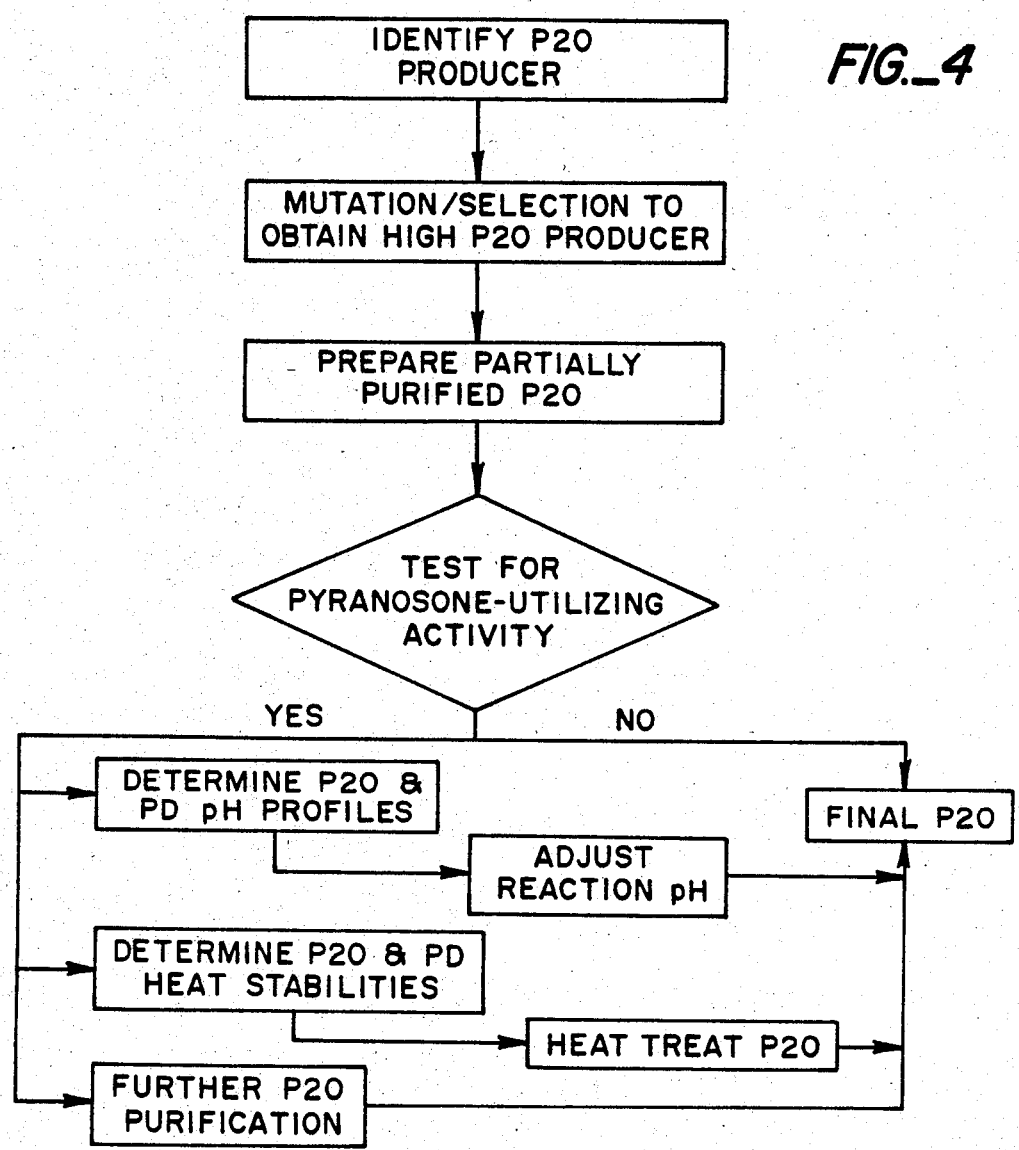
FIG._4
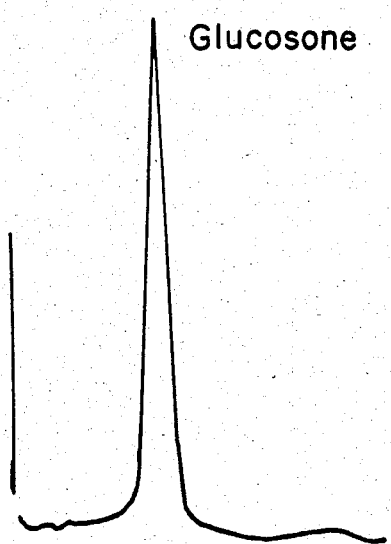
FIG._5

FUNGAL PYRANOSE-2-OXIDASE PREPARATIONS

BACKGROUND AND SUMMARY

The present invention relates to methods and reagents for obtaining substantially pure products by enzymatic oxidation of the hydroxyl group at specific positions on certain pyranoses and structurally related compounds. In particular, the invention concerns improved processes and reagents for making D-glucosone from D-glucose, D-xylosone from D-xylose, 5-keto-D-fructose from L-sorbose, or a mixture of 2-keto-D-gluconic acid and D-isoascorbic acid from delta-D-gluconolactone by reacting D-glucose, D-xylose, L-sorbose or delta D-gluconolactone, respectively, with oxygen in aqueous solution at a pH between about 4 and 7 in the presence of a pyranose-2-oxidase enzyme. The invention also concerns pyranose-2-oxidase enzymes and fungi which are sources thereof. Finally, the invention pertains to pyranosone-utilizing enzymes often found in pyranose-2-oxidase enzyme preparations obtained from certain fungal sources.

As used herein:

Glucose means D-glucose.

Glucosone means D-glucosone, also known as D-arabino-2-hexosulose.

Fructose means D-fructose.

Xylose means D-xylose.

Xylosone means D-xylosone, also known as D-threo-2-pentasulose.

Xyulose means D-xyulose, also known as D-threo-2-pentulose.

Sorbose means L-sorbose.

5-ketofructose means 5-keto-D-fructose, also known as D-threo-2,5-hexodiulose.

Delta-gluconolactone means delta-D-gluconolactone, also known as D-gluconic acid delta-lactone.

2-ketogluconic acid means 2-keto-D-gluconic acid.

Isoascorbic acid means D-isoascorbic acid, also known as D-araboascorbic acid.

Pyranose means glucose, xylose, sorbose or delta-gluconolactone.

Pyranosone refers to glucosone or xylosone.

NRRL means the culture depository of the United States Department of Agriculture Northern Regional Research Laboratory in Peoria, Ill., U.S.A. All NRRL deposits referred to herein were made under the terms of the Budapest Treaty on the International recognition of the Deposit of Microorganisms for the Purposes of Patent Procedure and Regulations promulgated thereunder.

ATCC refers to the American Type Culture Collection culture depository located in Rockville, Md., U.S.A.

CMCC refers to the private culture collection of Cetus Corporation, 1400 Fifty-Third St., Emeryville, Calif., U.S.A.

There is commercial interest in producing substantialy pure pyranosones by enzymatic conversion of corresponding pyranoses. In part, this interest has grown out of recent advances in fructose production in which glucosone is made as an intermediate. U.S. Pat. No. 4,246,347, assigned to the assignee of the present application and incorporated herein by reference, discloses a fructose-production method comprising enzymatic conversion of glucose to glucosone, followed by catalytic hydrogenation of gglucosone to fructose. In order to produce fructose at a purity suitable for use as a food sweetener, it is necessary that the intermediate glucosone also be substantially pure.

Glucosone also has application in the production of mannitol and sorbitol. U.S. patent application Ser. Nos. 409,990, filed Aug. 20, 1982, now abandoned and 517,996, filed Aug. 1, 1983, entitled "Process for the Production of Mannitol and Sorbitol", also assigned to the assignee of the present application and incorporated herein by reference, describe a method of producing a mixture of mannitol and sorbitol having an exceptionally high mannitol-to-sorbitol ratio. The mixture is prepared by reducing a solution of glucosone by catalytic hydrogenation, using a nickel catalyst in the presence of hydrogen. For production of a mannitol/sorbitol mixture suitable for use as a food sweetener, substantially pure glucosone must be used.

Glucosone, being a relatively reactive compound, is also expected to be of use in other synthetic processes. For example, glucosone in aqueous solution at pH between about 4.5 and about 8.5 (preferably between pH 6.0 and 6.5) can be converted, by a novel pyranosone dehydratase enzyme described herein, to the antibiotic cortalcerone (2-hydroxy-6H-3-pyrone-2-carboxaldehyde hydrate, see Baute, et al., Phytochemistry 15, 1753–1755 (1976); Baute, et al., Phytochemistry 16, 1895–1897 (1977)).

This pyranosone dehydrates enzyme first catalyses the dehydration of two of the equilibrium forms of glucosone present in aqueous solution, alpha-D-arabino-hexosulopyranose and/or beta-D-arabino-hexosulopyranose, to 2,4-dihydroxy-6-hydroxymethyl-6H-3-pyrone (and tautomers thereof). The equilibrium forms of glucosone which are substrates for the pyranosone dehydratase both have a keto group at position 2 in the pyranose ring, an R configuration at carbon 4 in the pyranose ring (the same stereochemical configuration as at carbon 4 in D-glucose), and an axial hydrogen at carbon 3 (disposed with respect to the pyranose ring in the same way as the hydrogen at carbon 3 in D-glucose). This arrangement of keto oxygen at position 2, hydroxyl at position 4, and hydrogen at position 3 of a pyranose ring apparently provides the substrate specificity for catalytic dehydration (involving removal of the hydroxyl from position 4, and hydrogen from position 3) by pyranosone dehydratase. (A hydroxyl group at carbon 1 might also be required for substrate specificity.)

For formal names of sugars and sugar derivatives used in the present specification, reference is made to R. Shallenberger, Advanced Sugar Chemistry: Principles of Sugar Stereochemistry, AVI Publishing Company, Inc., Westport, Conn., 1982, pp. 1–28. For determination of configuration at chiral centers according to the R.S. system, reference is made to J. Roberts and M. Casserio, Basic Principles of Organic Chemistry, W. A. Benjamin, Inc., New York, N.Y., 1964, pp. 592–593.

The intermediate, 2,4-dihydroxy-6-hydroxymethyl-6H-3-pyrone is named by analogy with the formal name for cortalcerone, provided in Baute (1976), supra. The oxygen in the pyrone ring is at position 1, the keto-carbon at position 3 and the double bond between positions 4 and 5.

This intermediate has a highly strained structure. Its ring opens spontaneously in aqueous solution, forming 4-deoxy-aldehydro-D-glycero-2,3-hexadiulose and tautomers thereof. The compound, and its tautomers, can recyclize between carbons 2 and 6 to form 3-deoxy-D-glycero-pentosulopyranose, 1-carboxaldehyde. This compound, which has the required steric arrangement for catalytic action by pyranosone dehydratase (an equitorial hydroxyl group on carbon 4, an axial hydrogen on carbon 3, and a keto oxygen on carbon 2) can be catalytically dehydrated by the enzyme to remove the hydroxyl from carbon 4 and one of the hydrogens from carbon 3, to produce cortalcerone, an antibiotic.

Another use of glucosone is described in U.S. Pat. No. 4,351,902, assigned to the assignee of the present application and incorporated herein by reference. The patent describes the catalytic oxidation of glucosone by glucose-1-oxidase to form 2-ketogluconic acid, which has uses in food and other industries.

The other pyranosone which can be prepared as described herein is xylosone. Xylosone can be reduced to xyulose by known methods, particularly by hydrogenation with molecular hydrogen in the presence of a heavy metal catalyst (e.g. palladium or carbon), and by other methods, as described, for the reduction of glucosone by fructose, in U.S. Pat. No. 4,246,347 and Geigert, et al., Carbohyd. Res. 113, 159–162 (1983). Xyulose can be fermented to ethanol by common yeasts (e.g. *Saccharomyces cerevisiae*), which are essentially incapable of fermenting xyulose, a major by-product of biomass degradation. See Wang, et al., Biochem. and Biophys. Rsch. Commun. 94, 248–253 (1980); Chiang, t al., Appl. and Environ. Microbiol. 42, 284–289 (1981). Thus, the methods and reagents of the present invention for conversion of xylose to xylosone, without subsequent significant enzymatic reaction of the xylosone, provide one step in a process for utilizing xylose from biomass to make ethanol.

The novel pyranosone dehydratase enzyme, whose catalysis of the dehydration of glucosone to cortalcerone is described above and whose properties and isolation are further described below, also catalyzes the dehydration of xylosone in aqueous solution to compounds which would be expected to have antibiotic properties similar to cortalcerone, and potentially other properties which make them useful to the fungi which produce them, starting from xylose and passing through xylosone, under conditions of stress.

Xylosone exists in aqueous solution as an equilibrium mixture of alpha, D-threo-pentosuloplyranose and beta, D-threo-pentosulopyranose. These compounds are the analogues of the alpha and beta anomers of the form of glucosone in solution on which the pyranosone-dehydratase acts, as described above. The xylosones differ from the glucosones by the absence of an hydroxymethyl group at carbon 5 in the pyranose ring. The pyranosone dehydratase one or both equilibrium forms of xylosone to 2,4-dihydroxy-6H-3-pyrone (and tautomers thereof).

2,4-dihydroxy-6H-3-pyrone is, like its analog derived from glycosone, a highly strained compound. It likely ring-opens to 4-deoxy-aldehydo-2,3-pentadiulose and tautomers thereof. The compound and any of the tautomers may be hydrated at the aldehyde group at position-1.

Because 4-deoxy-aldehydo-2,3-pentadiulose lacks a sixth carbon atom, it cannot rearrange into a form with the steric requirement, described above, for the action of pyranosone dehydratase. Consequently, the enzyme dehydrates xylosone only once.

Both 2,4-dihydroxy-6H-3-pyrone, and its 6-hydroxymethyl analog have absorbance maxima in the UV at about 265 nm. 4-deoxy-aldehydo-2,3-pentadiulose (or tautomers or aldehyde-group hydrates of the compound) and 4-deoxy-aldehydo-D-glycero-2,3-hexadiulose (or tautomers or aldehyde-group hydrates of the compound) might absorb strongly near 265 nm, but do not absorb significantly at any other wavelength between about 200 nm and about 300 nm. 3-deoxy-D-glyceropentosulopyranose, 1-carboxaldehyde (in any configuration, whether hydrated or not) does not absorb in the UV between about 200 nm and about 300 nm. Cortalcerone, however, has an absorption maximum only at about 230 nm, between 200 and 300 nm. Thus, adding pyranosone dehydratase enzyme to an aqueous solution of pure xylosone results in increasing absorption at 265 nm and no absorption at 230 nm as the xylosone is dehydrated to the 6H-3-pyrone. However, adding pyranosone dehydratase enzyme to an aqueous solution of pure glucosone results first in increasing absorption at 265 nm, as glucosone is dehydrated to the 6H-3-pyrone, and eventually in increasing absorption at 230 nm and decreasing absorption at 265 nm as 6H-3-pyrone rearranges to non-UV-absorbing 3-deoxy-D-glycero-pentosulopyranose, 1 carboxaldehyde, which in turn is dehydrated by the enzyme to cortalcerone.

The 5-ketofructose obtained in substantially pure form from sorbose, with the methods and reagents provided in the present specification, can be converted to kojic acid, 3-oxykojic acid and 5-oxymaltol. See, e.g. Sato, et al., J. Agr. Biol. Chem. 31, 877–878 (1967) and 33, 1606–1611 (1969). Kojic acid itself is an antibiotic and can be converted to the flavor-enhancing additives maltol and ethyl maltol. See Merck Index, 10th Edition, p. 764 (1983).

The uses of mixtures of 2-ketogluconic and isoascorbic acids provided from delta-gluconolactone by the methods and reagents of the present specification are set forth in U.S. Patent 4,351,902, supra.

The production of pyranosones, 5-ketofructose and mixtures of 2-ketogluconic and isoascorbic acids from the corresponding pyranoses using a pyranose-2-oxidase enzyme preparation from *P. obtusus* has been described, e.g., Janssen and Ruelius, Biochim. et Biophys. Acta 167, 501–510 (1968). Above-mentioned U.S. Pat. Nos. 4,246,347, 4,321,323, 4,321,324 and 4,423,149 describe production of glucosone from glucose using glucose-2-oxidase enzyme preparations from various Basidiomycetes.

U.S. Pat. No. 4,423,149 is assigned to the assignee of the present application and is incorporated herein by reference. Above-mentioned U.S. Pat. Nos. 4,351,902 and 4,423,149 describe production of mixtures of 2-ketogluconic and isoascorbic acids from deltagluconolactone using glucose-2-oxidase enzyme preparations from Basidiomycetes. The prior art references in this area describe reactions using partially purified pyranose-2-oxidase (P2O) derived from *Polyporous obtusus*, and carried out at a preferred pH of about 7.0. For a variety of reasons which will be explored below, these reaction methods inherently produce breakdown of the pyranosone products, reducing the yield and purity. The prior art methods are also characterized generally by relatively short P2O half lives, due in part to a failure to control co-produced $H_2O_2$ levels adequately, as will be seen below.

It is therefore one general object of the present invention to provide a method and reagent by which pyranoses can be enzymatically oxidized to the corresponding pyranosones or related compounds with substantially greater yield and purity than is obtainable by prior art methods and reagents.

A particular object of the invention is to provide a method of producing substantially pure glucosone for use in making high-purity food additive sugars such as fructose, mannitol and sorbitol.

Yet another object of the invention is to provide a relatively inexpensive and easily prepared P2O reagent which has enhanced stability under the reaction conditions employed in the method of the invention.

Providing a reagent and method which are readily adaptable to commercial-scale uses is still another object of the invention.

The method of the invention includes providing a P2O enzyme or enzyme preparation which is substantially free of measurable pyranosone-utilizing enzyme activity at a selected pH between about 4.4 and 7.0. The P2O preparation is reacted with a pyranose substrate in the presence of an $H_2O_2$-removing catalyst, such as catalase. A preferred $H_2O_2$-removing catalyst includes catalase which has been purified to remove substantially all glucose-1-oxidase activity. The reaction is performed in the presence of oxygen at the selected pH between 4.4 and 6.0.

One major pyranosone-utilizing enzyme which has been identified is referred to herein as pyranosone dehydratase (PD), so called for its ability to dehydrate pyranosones such as glucosone and xylosone. This enzyme is present in partially purified P2O enzyme preparations obtained from *P. obtusus*. The activity of the enzyme may be substantially eliminated, according to one aspect of the invention by (a) purifying the P2O preparation to remove PD; (b) heat-treating the P2O preparation to inactivate PD preferentially; and/or (c) carrying out the reaction at about pH 4.4.

The invention also contemplates selecting, as a source of P2O, a fungal organism which is capable of converting glucose to glucosone, evidencing a P2O enzyme, but which is incapable of converting glucose or glucosone to cortalcerone, evidencing the absence of PD. Two preferred organisms include *Coriolus versicolor* and *Lenzites betulinus*.

In one embodiment of the invention, there is provided a reagent composed of a solid support and surface-attached P2O and catalase molecules, at a P2O/catalase activity ratio of between about $10^{-5}$ to $10^{-3}$. The P2O is prepared to be free of substantially all pyranosone utilizing enzyme contaminants at a selected pH between about 4.4 and 6.0.

The invention also contemplates substantially pure P2O enzymes prepared from the above-mentioned sources, as well as cultures of fungi which produce enhanced amounts of P2O enzyme.

These and other objects and features of the invention will become more fully apparent from the following description of the invention, when read in conjunction with the accompanying drawings.

BRIEF DESCRIPTION OF THE DRAWINGS

FIG. 1 compares the kinetics of heat inactivation of partially proteolyzed and intact forms of P2O and PD obtained from *P. obtusus*;

FIG. 2 shows the pH profile of *P. obtusus* P2O and PD;

FIG. 3A is an absorbance profile, at 192 nm, of HPLC-fractionated reaction products obtained by reacting glucose, at pH 6.0, with a partially purified *P. obtusus* P2O enzyme preparation;

FIG. 3B is an absorbance profile, like that in FIG. 3A, of reaction products produced by reacting glucose at pH 6.0 with a *P. obtusus* P2O enzyme which has been purified to remove glucosone-utilizing enzyme contaminants;

FIG. 3C is an absorbance profile, like that in FIG. 3A, of reaction products produced by reacting glucose at pH 6.0, with a *P. obtusus* P2O enzyme preparation which has been heat-treated to inactivate glucosone-utilizing enzyme contaminants;

FIG. 3D is an absorbance profile, like that in FIG. 1A, of reaction products produced by reacting glucose, at pH 4.4, with the P2O enzyme preparation of FIG. A;

FIG. 3E is an absorbance profile, like that shown in FIG. 3A, where the reaction described in FIG. 3B was performed at pH 4.4;

FIG. 4 illustrates, in flow-diagram form, procedures used in providing a P2O enzyme in accordance with the invention; and FIG. 5 shows an absorbance profile, at 192nm, of HPLC-fractionated reaction products obtained by reacting glucose, at pH 5.0, with purified *P. obtusus* P2O in an unbuffered reaction medium.

DETAILED DESCRIPTION OF THE INVENTION

The invention includes providing a P2O enzyme, or enzyme preparation which is substantially free of pyranosone-utilizing enzyme contaminants which are measurably active at a selected pH between about 4.4 and 7.0. The P2O enzyme may be used in forming a reagent which also includes an $H_2O_2$-decomposing catalyst, such as catalase, at a P2O/catalase activity ratio of less than about $10^{-3}$, i.e., an $H_2O_2$ concentration of less than about $10^{-3}$ M. The enzyme, or enzyme reagent, is reacted with a pyranose substrate in the presence of oxygen, at the selected pH to produce the corresponding, substantially pure product glucosone, xylosone, 5-ketofructose or mixture of 2-ketogluconic acid and isoascorbic acid. Preferred substrates are glucose and xylose; most preferred is glucose. The reaction may be pH stable, even in an unbuffered reaction medium. Details of the invention will be described below with particular reference to methods for providing a P2O enzyme, for producing a reagent containing the enzyme and an $H_2O_2$-decomposing catalyst, and to reaction methods using the enzyme to produce substantially pure pyranosones, particularly glucosone.

Providing a P2O Enzyme

As used herein, the terms "pyranose-2-oxidase" or "P2O" designates an enzyme capable of catalyzing the conversion, in aqueous solution with oxygen as co-reactant and hydrogen peroxide as co-product, of the hydroxyl group at the second carbon position (in the cases of glucose, xylose and deltagluconolactone) or the fifth carbon position (in the case of sorbose) of a pyranose to a keto group. The enzyme's preferred substrate is glucose, which is converted to glucosone; but the enzyme also is active in converting xylose to xylosone, sorbose to 5-ketofructose and delta-gluconolactone to a mixture of 2-ketogluconic and isoascorbic acids.

Enzymes displaying such pyranose-2-oxidase activity may be obtained from a variety of microorganisms, molusca and red algae, as reported in the above cited U.S. Pat. No. 4,246,347. Among the preferred sources of the enzyme are the white-rot fungi of the Basidiomycetes class, including *Polyporus obtusus, Coriolus versic-*

*olor*, and *Lenzites betulinus* organisms, expecially *P. obtusus*. These fungal organisms produce P20 enzymes having a preferred substrate specificity for glucose and an additional substrate specificity for sorbose, xylose and delta-gluconolactone.

The amount of pyranose-2-oxidase enzyme produced by the selected organism may be increased by mutation and selection techniques. Typically, cells which have been prescreened for ability to produce relatively high P20 levels are exposed to a mutagenic agent, such as ultraviolet light, at a preselected level. Following exposure to the mutagen, the cells are individually selected for increased P20 activity. The mutation/selection procedure may be repeated to yield still higher-producing strains. Example I below details a mutation/selection protocol used to produce a *P. obtusus* strain which produces P20 at a level which is about 5 times that of the unmutated *P. obtusus* cells prior to the selection procedure.

A P20 enzyme preparation containing partially purified P20 is prepared by disrupting cells of the selected organism, and removing insoluble cell material by centrifugation. Further enzyme purification is achieved by adding to the supernatant, an agent which produces precipitation of selected supernatant proteins. Exemplary protein-precipitating agents including salts, such as ammonium sulfate, solvents, such as polyethylene glycol, and strong acids. The agent may be added at a single concentration, or in a series of increasing concentrations. The precipitated proteins, which may include P20, are removed by centrifugation or filtration.

The P20 enzyme derived from *P. obtusus* and *L. betulinus* are preferably fractionated by precipitating the enzymes by the addition of polyethylene glycol. Ammonium sulfate precipitation of the *C. versicolor* P20 enzyme is preferred. The enzyme precipitates may be resuspended in a buffer, incubated, and recentrifuged to remove insoluble proteins remaining in the resuspended enzyme fraction.

Partially purified P20 enzyme preparations obtained from *P. obtusus* have been reported in the prior art. Janssen and Ruelius (1968) and U.S. Pat. Nos. 4,246,347; 4,351,902; and 4,423,149, supra. These patents disclose a partially purified pyranose-2-oxidase fraction obtained from *P. obtusus*, substantially according to the purification steps outlined above. The enzyme preparation is advantageous in that *P. obtusus* is known to produce relatively high levels of P20, and the enzyme can be obtained in large quantity from fermenting cells. The steps leading to the partial enzyme purification can be carried out in commercial-scale quantitites at relatively low cost, since only low-speed centrifugation steps are involved.

However, a variety of studies in which the above partially purified *P. obtusus* P20 was used to convert glucose have shown that the glucosone produced may be contaminated to a substantial degree with by-products. In one typical reaction study, reported in detail in Example II below, a partially purified *P. obtusus* P20 enzyme was reacted with a solution of pure glucose in a 0.1M sodium phosphate buffer, pH 6.0 in the presence of oxygen. $H_2O_2$ generated in the reaction was decomposed by purified catalase also added to the reaction medium. The glucose was completely used up after a 2 hour reaction time at 24° C. However, the reaction was carried out for 6 hours at room temperature, to accentuate glucosone conversion of degradation reactions which contribute to reaction impurities. The pH of the buffered reaction medium remained constant over the reaction period.

The products were analyzed by high performance liquid chromatography (HPLC) as described in Example II. The eluate from the column was monitored at 192 nm, where both glucosone (which absorbs strongly below 200 nm) and by-products (which absorb strongly about 230 nm), are detectable. The absorbance profile of the reaction products, seen in FIG. 3A, shows a peak which co-elutes with authentic glucosone and a major peak representing non-glucosone by-products. The relatively high ratio of by-products to glucosone observed is somewhat exaggerated over what would be observed in an optimal-condition reaction, due to the extended time period of the reaction as noted above.

Heretofore, investigators in the field of the invention believed that the major cause of by-product formation observed in the enzymatic conversion of glucose to glucosone was due to chemical instability of the glucosone. Thus previous attempts to increase product yield and purity of enzymatically produced glucosone centered on improving reaction conditions to increase the chemical stability of the product formed, and to reduce the timing during which product decomposition could occur.

An important feature of the present invention is the finding that a major part of the non-glucosone by-products observed in an enzymatic glucosone-production reaction is due to the presence in the P20 enzyme preparation of one or more pyranosone-utilizing enzyme contaminants. Studies have led to the identification of one major, and perhaps sole, pyranosone-utilizing enzyme contaminant in P20 preparations from the fungal source, *P. obtusus*. The contaminating enzyme functions to dehydrate pyranosones, and accordingly has been designated "pyranosone dehydratase." Of particular interest is the action of this enzyme on glucosone. Initial enzymatic dehydration of glucosone produces an unstable intermediate which has an absorption peak at about 265 nm. The intermediate then rearranges to a stable pyranosone intermediate which is further enzymatically dehydrated, by the same enzyme, to form the antibiotic cortalcerone, as discussed above. One of the functions of P20 in some organisms, therefore, may be to produce glucosone for use in the enzymatic synthesis of cortalcerone by PD.

The PD enzyme acts also with xylosone to produce a product which also absorbs with a peak near 265 nm. This product is the analog, (lacking a hydroxymethyl group at position 5 on the pyrone ring) of the first intermediate formed from glucosone by the PD enzyme. Like the first intermediate from glucosone, xylosone product intermediate may rearrange by ring-opening. However, because it has six carbon atoms, the ring-opened form of the intermediate from glucosone can undergo ring closure to a form with the steric requirements for the PD enzyme act (i.e. dehydrate) again, resulting in cortalcerone. However, the straight-chain form of the xylosone-derived intermediate, having 5 carbons, cannot recyclize to a form that can be acted on further by the PD enzyme. The product of PD action on xylosone may also be an antibiotic. Thus, the role of P20 is some organisms might also be to provide xylosone for subsequent dehydration with PD to provide an antibiotic for defensive purposes.

The method of the invention comprises, in part, providing a P20 enzyme which is substantially free of pyranosone-utilizing enzyme contaminants which have measurable activity at a selected pH between about 4.4 and 7.0. A first step in providing the enzyme involves selecting a suitable P20 source. Preferred P20 sources include microorganisms, and particularly fungal organisms, which can be cultured in relatively large quantities in a relatively short time period. A microorganism, such as a fungus, which produces P20 can be identified readily by the ability of the cells, when broken, to convert glucose to glucosone, as determined, for example, by the reaction of glucosone with triphenyltetrazolium chloride (TTC) to give a strongly colored solution. By way of illustration, a parental (unmutated) strain of *P. obtusus* was found to produce between about 200 and 500 enzyme units per liter of fungal culture after a ten day culture period. Parental strains of *C. versicolor* and *L. betulinus* each produced between about 50 and 100 units per liter of fungal culture after a 7-day culture period.

Having identified a suitable microbial source of P20, according to the above screening procedure, the organism is then tested, in a broken-cell assay, for its ability to convert glucosone to cortalcerone, indicating the presence of PD. The conversion of glucosone to cortalcerone can be monitored spectrophotometrically by following the reaction at the cortalcerone absorption peak at about 230nm, or at 265 nm, where an intermediate between glucosone and cortalcerone produced by PD from glucosone absorbs. Alternatively, the disappearance of glucosone as monitored, for example in the above TTC-colorometric assay, may be used to screen for PD activity, and more generally, for glucosone-utilizing enzyme activity. Among the three Basidiomycetes listed above which were found to produce P20, only *P. obtusus* showed measurable PD activity. The above selection procedure is thus seen to identify two general categories of P20 producing organisms: one having the ability to convert glucose to glucosone and glucose or glucosone to cortalcerone, the latter reaction evidencing the presence of PD, and a second group capable of converting glucose to glucosone, but incapable of further metabolizing glucosone to cortalcerone. These screening procedures could also be carried out using xylose and xylosone in place of glucose and glucosone, as xylosone can also be assayed using the TTC assay and is also dehydrated by PD to a spectrophotometrically active product, which absorbs strongly at about 260 nm.

Where the organism selected includes both glucosone-producing and glucosone-utilizing enzymes, the invention further contemplates providing a P20 enzyme which is substantially free of all measurable glucosone-utilizing enzyme activity at a selected pH between about 4.4 and 7.0. Initially a partially purified P20 preparation is obtained. Novel procedures for freeing the P20 enzyme preparation of pyranosone-utilizing enzyme activity at such selected pH generally include one of the following procedures:

(a) The P20 enzyme is purified to remove substantially all pyranosone-utilizing enzymes, and in particular PD, which are active at a pH of about 6.0 or below;

(b) The P20 enzyme is heat-treated to eliminate substantially all pyranosone-utilizing enzyme activity at a pH below about 6.0; and (c) The P20 enzyme is utilized at a pH at or near about pH 4.4

Although the three procedures discussed above will be described with particular reference to a P20 enzyme fraction obtained from *P. obtusus*, it will be appreciated that the rationale underlying each of the procedures will be applicable to P20 enzyme preparations obtained from other sources.

Further purification of the enzyme preparation, in accordance with procedure (a) above, is preferably carried out by ion-exchange chromatography. The chromatographic separation can be monitored readily by assaying the eluted fractions for both P20 and PD activity. The eluted samples are preferably assayed at a maximum pH of about 6.5. The eluted samples showing highest P20 activity are combined, and where necessary, further separated from PD activity by molecular-sieve chromatography. The reaction scheme used to purify *P. obtusus* P20 substantially to homogeneity is detailed in Example III below.

To test the ability of the purified P20 enzyme to produce substantially pure pyranosone, a reaction study similar to the one described above, where the enzyme is used to convert glucose to glucosone in the presence of purified catalase at pH 6.0, is performed. Example IV below gives details of experimental procedures used and results obtained, with reference to FIG. 3B. As can be appreciated from this figure, the glucosone produced, after a six hour incubation period at pH 6.0, is substantially free of by-products, showing that most, if not all, glucosone breakdown at pH 6.0 is attributable to enzymatic breakdown.

Heat-treating the P20 enzyme preparation to inactivate pyranosone-utilizing enzyme contaminants, as in procedure (b), may be preferred where the P20 is substantially more heat-stable than pyranosone-utilizing enzyme contaminants. Heat inactivation can be performed relatively simply and inexpensively by comparison with chromatographic purification techniques. In assessing the heat stability of the P20 enzyme, the effect of partial proteolysis and pH should be considered. For example, studies on the heat stability of P20 obtained from *P. obtusus* show that the enzyme is readily proteolyzed following cell homogenization, and that the partially proteolyzed enzyme is more heat labile than the intact enzyme. Accordingly, it is advantageous to prepare the enzyme in the presence of proteolytic inhibitors such as phenylmethylsufonyl fluoride (PMSF) and/or ethylenediamine tetraacetic acid (EDTA).

The relative thermal stabilities of P. obtusus P20 isolated either in the presence or absence of proteolytic inhibitors is shown in FIG. 1. As seen here, a P20 preparation which is largely unproteolyzed loses only about 20% of its total activity over a 90 minute incubation time at 65° C., at pH 5.0, while the partially proteolyzed enzyme loses more than half its activity under similar conditions. Also as seen in this figure, purified *P. obtusus* PD lost substantially all of its activity after 15 minutes of incubation at 65° C. Details of the heat-treatment studies are found in Example V.

The effect of heat-treating a P20 enzyme preparation under selected conditions can be determined by reacting the heat-treated enzyme with glucose under conditions substantially identical to those which have been described above with reference to FIGS. 3A and 3B. Example VI provides details of a reaction employing a heat-treated P20 preparation obtained from *P. obtusus* in the absence of protease inhibitors. The reaction products, fractionated by HPLC and monitored at 192 nm, gave the absorption profile seen in FIG. 3C. The yield and purity of the glucosone produced using the heat-treated enzyme is substantially improved over the results obtained using an untreated P20 preparation, and the improvement is expected to be still greater where protease inhibitors are added to the P20 preparation, and the length and/or temperature of the heating step is increased to produce greater inactivation of the pyranosone-utilizing enzyme(s).

The P20 obtained from *P. obtusus* is more resistant to heat inactivation than the P20 obtained from either *C. versicolor* and *L. betulinus*. On the other hand the *C. versicolor* and *L. betulinus* P20 enzymes appear to be more protease-resistant. It can be appreciated that purification to remove enzyme contaminants would be preferred for protease-resistant P20 enzymes, whereas heat-treatment would be advantageous for more heat-resistant P20 enzymes.

In procedure (c), pyranosone-utilizing enzyme activity in a P20 enzyme preparation is eliminated by utilizing of the enzyme at about pH 4.4. The method stems from the discovery that, for some P20 preparations, product-utilizing enzymes are largely inactive, but P20 has near maximal activity, at this pH. The suitability of the method, when compared with P20 purification or heat treatment may vary with the P20 source. To assess the value of this approach, pH activity profiles for P20 and glucosone-utilizing enzymes are determined. Example VII below details methods used to determine the pH profiles of *P. obtusus* P20 and PD. The results, which are graphed in FIG. 2, show that P20 has a pH optimum between about 4.5 and 5.5., that the pH optimum of PD is about 7.5, and the PD retains less than about 5% of its optimal activity at pH 4.4.

The ability of a P20 preparation to produce substantially pure product at pH 4.4 can be tested in the already-described reaction system involving the enzymatic conversion of glucose to glucosone. Details of a typical experiment to determine glucosone purity and yield at pH 4.4, using the above *P. obtusus* P20 preparation, are given in Example VIII. HPLC analysis of the reaction products monitored at 192 nm is shown is FIG. 3D. Here it is seen that performing the reaction at a pH at which at least one major glucosone-utilizing enzyme (PD) is substantially inactive leads to the production of a substantially pure glucosone. The results indicate that glucosone-utilizing enzyme contaminants, if any, other than PD are also substantially inactive at pH 4.4.

It can be appreciated that the above methods used to eliminate product-utilizing enzyme contaminants in the pyranose-2-oxidase enzyme preparation can be combined, where desired, to increase product purity and yield. For example, the P20 preparation may be fractionated to remove product-utilizing enzymes and the purified P20 then used in a reaction which is carried out at pH 4.4. Example IX below describes such a reaction for producing glucosone from glucose. The HPLC analysis of the reaction products is shown in FIG. 3E. The glucosone produced in the reaction is greater than 99% pure, as determined by relative peak areas obtained following HPLC, as measured by both refractive index and ultraviolet absorption at 192 nm.

According to another embodiment of the invention, a P20 enzyme which is substantially free of pyranosone-utilizing enzyme contaminants may be provided by selecting, as a source of the P20 enzyme, a microorganism which is capable of converting glucose to glucosone, but is unable to convert glucose or glucosone to cortalcerone. This selection procedure identifies microorganisms which synthesize P20 but little or no PD. The organism is screened for the ability to convert glucose to glucosone and glucosone to cortalcerone by conventional assay methods, such as those referred to above. Example X describes specific procedures used in selecting two fungal organisms, *C. versicolor* and *L. betulinus*, which produce moderate levels of P20, but which lack the ability to convert glucosone to cortalcerone.

A purified or partially purified P20 enzyme is obtained from the selected source lacking measurable PD activity. Generally, the P20 purification procedure comprises (1) obtaining a cell supernatant fraction containing the P20 enzyme, and (2) selectively precipitating the P20 with a protein-precipitating agent such as ammonium sulfate or polyethylene glycol. Where necessary, the P20 enzyme may be further purified by chromatographic techniques, such as ion-exchange and/or molecular sieve chromatography.

Examples XI and XII below outline purification procedures used to obtain substantially pure P20 from *C. versicolor* and *L. betulinus*, respectively. P20 obtained from *L. betulinus* was assayed for its ability to convert glucose to glucosone in a reaction containing 20 mM glucose, catalase, and oxygen, in a suitable buffer. After a two-hour reaction period, the products were fractionated by HPLC as monitored at 192 nm. Products analysis showed tht the glucosone produced was substantially pure.

FIG. 4 presents, in flow-chart format, a general procedure for providing a P20 in accordance with the invention, based on the findings presented above. The first step in the procedure is to identify microbial P20 producers, such as the three fungal sources of P20 discussed herein.

Considering the scheme shown in FIG. 4, the organism may be carried through one or more mutation and selection steps, such as described in Example I, to produce strains which produce elevated levels of P20 and/or enhanced P20/PD ratios. An especially advantageus strain obtained by mutagenesis and selection is *P. obtusus* strain AU124, cultures of which have been deposited at NRRL under No. 15595.

A partially purified P20 enzyme is obtained by batch purification techniques which preferably involve selective protein precipitation and centrifugation steps only. The partially purified P20 is then assayed for pyranosone-utilizing activity, e.g., by the ability of the enzyme preparation to convert glucose to substantially pure glucosone at about 6.0. If no pyranosone-utilizing activity is observed in this indirect assay, or in a direct PD activity assay monitored at either 230 or 265 nm, the preparation may be suitable for use as a "final" P20 enzyme in accordance with the invention. Such might be the case, for example, where the P20 preparation is obtained from a selected source such as *C. veriscolor* or *L. betulinus* which does not show measurable PD activity on initial screening.

Where, as with the P20 enzyme preparation obtained from *P. obtusus*, relatively high levels of product impurities are observed, e.g., by HPLC analysis, evidencing high PD activity at pH 6.0, the contamining enzyme activity is substantially eliminated by one or more of the three procedures described. In one procedure, the enzyme preparation is utilized at a pH at which P20 activity is optimal or near-optimal, but at which pyranosone-utilizing enzyme(s) are largely inactive. In a second procedure, the P20 preparation is heat treated to inactivate pyranosone-utilizing enzymes preferentially. Both methods are suited to large-scale processes and are rapid and inexpensive, making them attractive for commercial-scale preparation of a P2O enzyme.

Where necessary, the P2O preparation can be further purified to remove product-utilizing enzyme contaminants. The findings presented above suggest that PD is the major, if not the only, pyranosone-utilizing enzyme in the *P. obtusus* P2O enzyme preparation. Therefore, the purification method can focus on removal of PD only, simplifying the procedure.

Preparing Immobilized P2O Reagent and Controlling Peroxide

The conversion of a pyranose to the corresponding pyranosone by P2O in the presence of oxygen is accompanied by the stoichiometric production of $H_2O_2$. The $H_2O_2$ produced in the reactin may promote oxidative degradation of the product. Studies performed in support of the present application indicate that nonenzymatic breakdown of glucosone to acidic products may be accelerated at $H_2O_2$ concentrations above about 0.2 mM. More importantly, elevated $H_2O_2$ concentrations produce relatively rapid inactivation of the P2O enzyme. The susceptibility of P2O to inactivation by elevated concentrations of $H_2O_2$ in a continuous-flow reactor is described below in Example XIII. Briefly, four continuous-flow reactors containing different P2O/catalase activity ratios were run in the presence of pure glucose. The half-life of the P2O enzyme in each reactor was determined from the observed change in the amount of glucosone eluting from the reactor over a several-day reaction period. The measured half-lives of P2O expressed in arbitrary half-line units, are given in Example XIII, Table 1. As will be seen from the table, the presence of catalase, at a P2O/catalase activity ratio of less than about $10^{-3}$ and preferably less than about $2\times10^{-4}$ (i.e., at an $H_2O_2$ concentration of less than about 0.2 mM) extends the measured P2O half-life 30-fold with respect to that of P2O reacted with glucose in the absence of catalase.

The invention contemplates the use of a variety of peroxide-destroying catalysts to maintain the $H_2O_2$ concentration of the reaction medium at or below a desired level. These reagents include enzymes, such as catalase, or metal catalysts, such as platinum. A preferred catalyst includes catalase which has been freed of glucose-utilizing enzymes, such as glucose-1-oxidase, which are active in the pH 4.4 to 6.5 range. The catalase may be obtained from conventional sources, such as *Aspergillus niger*.

Since P2O is both the site of $H_2O_2$ production, and a target of $H_2O_2$ inactivation, it is important to prevent locally high $H_2O_2$ transients, in the vicinity of the P2O, as well as the buildup of $H_2O_2$ in the bulk phase. To this end, the catalyst is preferably disposed in close physical association with the P2O, preferably by coupling the P2O to a solid-support substrate having a surface-associated $H_2O_2$-decomposing catalyst. Intimate association between the oxidase enzyme and the catalyst on such a solid support is important particularly in a reactor system in which the medium is relatively unagitated, as in a packed reactor column.

A reagent constructed according to the invention includes a solid support and a surface array of molecules of P2O and an $H_2O_2$-decomposing catalyst. The support may include a broad range of surface-treated or untreated organic and inorganic supports. Included among these are polyacrylamide, ethylene maleic acid copolymers, methacrylic-based polymers, polypeptides, styrene-based polymers, agarose, cellulose, dextran, silica, porous glass beads, charcoal, hydroxyapatite and aluminum or titanium hydroxide.

Methods for attaching enzymes and non-protein catalysts to solid supports are well known and include adsorbing the enzyme to the support, or coupling by covalent attachment. A reagent containing both P2O and catalase is preferably formed by sequentially coupling catalase, then P2O to the support surface. Where the $H_2O_2$ decomposing catalysts is an inorganic catalyst, such as platinum, the reagent preferably is formed as a catalyst-coated solid support to which the P2O is attached.

In a commercial-scale reaction, the activity ratio of P2O to catalyst in the reagent is selected to make the operation most cost effective. Among the factors to be considered are the relative costs of the P2O and catalyst, the efficiency of the reaction at different P2O/catalyst activity ratios, the effect of $H_2O_2$ inactivation of the P2O and/or catalyst on the purity of the reaction product, and the purity and stability the product is required to have for the application(s) in which it is to be employed. As noted above, a P2O /catalase activity ratio of about $10^{-3}$ or less produces a relatively long P2O half-life in a continuous-reaction system.

Control Of Reaction pH

This section examines pH control in the method of the invention. As indicated above, the reaction is carried out at a selected pH between 4.4 and 7.0. The upper pH limit of 7.0 is based on two independent considerations: First, the P2O enzymes whose characteristics are reported herein, including the P2O obtained from *P. obtusus, L. betulinus* and *C. versicolor*, show pH optima generally in the pH 4.0 to 6.0 range, whereas the pyranosone-utilizing enzyme (PD) from *P. obtusus* appears to be most active near pH 7.5.

Secondly, studies indicate that pure glucosone undergoes relatively rapid, nonenzymatic breakdown above a pH of about 7.0. In one experiment, a 0.5% solution of highly purified glucosone (prepared by enzymatic conversion of glucose by a purified *P. obtusus* P2O enzyme at pH 4.4) was brought to pH 7.0 in a buffered solution. Immediately thereafter, the solution was scanned spectrophotometrically in the UV range between 200 and 350 nm, at one minute intervals. A slight peak observed initially at 310 nm continued to increase appreciably at each one minute interval, ultimately increasing several-fold over a five minute period, indicating rapid, nonenzymatic glucosone breakdown to a compound absorbing at 310 nm. In a similar experiment involving a 0.5% solution of glucosone at pH 6.0, no initial peak at 310 nm was observed nor did one form during the several-minute period during which one-minute interval scans were performed. Thus, non-enzymatic breakdown of glucose can be significantly reduced by maintaining a reaction pH of about 7.0 or below.

At pH's less than about 4.4, P2O and catalase activities decrease appreciably. It is seen in FIG. 2, for example, that *P. obtusus* P2O shows a sharp dropoff in activity between about pH 4.4 and pH 3.0. Similarly, catalase obtained from *A. niger* shows a sharp decline in activity below about pH 4.4.

Heretofore, enzymatically catalyzed glucose-to-glucosone reactions have been characterized by a gradual drop in pH during the course of the reaction. Previous studies on the chemical stability of glucosone by Ericsson, et al., *Cellulose Chem. Technol.* 7, 581 (1973), and by Lindberg, et al., *Acta Chem. Scand.*, 6, 1782 (1968), indicate that the observed pH drop may be due to nonenzymatic glucosone breakdown to sugar acids.

The pH drop observed in glucose-to-glucosone reactions carried out by prior art methods necessitates carrying out the reaction in a strong buffer and/or monitoring the reaction pH and adding a base periodically to offset acid formation. The reactions described above with reference to FIGS. 3A-3E employ 0.1M phosphate (pH 6.0) or citrate (pH 4.4) buffers, which were effective in maintaining the reaction pH constant over the 6-hour reaction periods used. However, in these reactions relatively low concentratios of substrates were used. Where higher concentrations of products are being generated in the reaction, stronger buffers would be required. However, a problem exists with the use of stronger buffers in that they may be incompatible with subsequent reactions used to convert the pyranosone product, such as glucosone, to the desired end product, such as fructose, mannitol or sorbitol. In addition, high salt concentrations are undesirable in food-grade products such as those. Finally, experiments conducted by the inventors have also shown that high-strength buffers may inhibit P2O activity.

Attempts to control reaction pH by the periodic addition of base have not been entirely successful. The above-referenced studies by Ericsson, et al. and Lindberg, et al., show that glucosone breaks down under alkaline conditions. Therefore, in order to reduce glucosone breakdown, the base must be added in a manner which minimizes local regions of high pH in the solution. The present inventors have found that controlling the reaction pH by adding NaOH periodically to maintain reaction pH leads to more glucosone breakdown than where a buffer such as 1M sodium bicarbonate or 1M TRIS-HCl is used. Introduction of the buffer with rapid mixing further reduces glucosone breakdown, presumably by reducing locally-elevated pH levels which occur when the buffer is added. It was noted above that even pH's in the range of 7.0 can lead to relatively rapid nonenzymatic glucosone breakdown. Ideally therefore, where high purity and yield are desired, one would like to avoid adding base to the reaction to offset the buildup of acidic by-products.

Heretofore, the enzymatic breakdown of enzymatically produced pyranosone to acidic by-products has not been considered as a primary mechanism of acid generation in reactions of the type considered herein. It is an important finding of the present invention, therefore, that reactions conducted in accordance with the method of the invention, in which substantially all pyranosone-utlizing enzyme activity is eliminated, do not show the characteristic drop in pH seen in glucosone-producing reactions known in the prior art. Accordingly, a reaction carried out using the method of the invention may be performed in an unbuffered or weakly buffered solution, without periodic addition of base, over extended reaction periods.

A reaction in which glucose is converted to glucosone by a substantially pure P2O, in the presence of purified catalase, without pH control, is described in Example XIV below. The reaction, involving the conversion of a 6% solution of glucose to glucosone, is carried out for 3 hours at room temperature in an unbuffered aqueous medium at pH 5.0. The pH remained constant during the reaction. HPLC analysis of the reaction products indicate that the glucosone produced was about 99% pure.

From the foregoing, several important advantages of the invention can be appreciated. The method of the invention provides a significant improvement in purity and yield over prior art methods for converting a pyranose such as glucose to a pyranosone, such as glucosone. The purity and yield improvement is especially important to the success of commercial reactions in which a pyranosone such as glucosone is used as an intermediate in the production of a food product.

Another important advantage in commercial production is that a suitable P2O preparation can be provided without involved enzyme purification procedures. In two P2O preparation methods described herein, no chromatographic purification techniques are used. In another, purification may involve selective removal of a pyranosone dehydratase enzyme only. In yet another, the source of P2O selected is one which lacks the major, and perhaps only, pyranosone-utilizing enzyme, PD.

Under the reaction conditions employed, generation of acidic by-products is substantially eliminated. The reaction can therefore be carried out over a several-hour period in an unbuffered reaction medium without addition of base.

A reagent constructed according to the invention includes a solid support having arrayed thereon molecules of P2O and $H_2O_2$-removing catalyst, at an activity ratio between about $10^{-5}$ and $10^{-3}$. This reagent has a half life which may be 30 to 60 times that of the P2O enzyme in a reaction where $H_2O_2$ levels are not controlled.

The following examples describe particular embodiments of making and using the invention, but are not intended to limit the scope of the invention.

EXAMPLE I

Selection of a *P. obtusus* strain which produces high levels of pyranose-2-oxidase This example describes the method used to produce a strain of *P. obtusus* which produces a level of P2O several times higher than that of the *P. obtusus* culture (ATCC 26733; NRRL 15592) from which the strain was derived. Mycelial pods of *P. obtusus*, ATCC No. 26733 also deposited by us at NRRL under No. 15592, and at CMCC under No. 0181, were grown on yeast/malt extract agar slants at pH 6.4, using standard yeast malt extract available from Diffco Laboratories (Detroit, Mich.) or agar prepared by mixing 3 g yeast extract, 3 g malt extract, 5 g peptone, 10 g glucose and 20 agar in 1 l of distilled water and autoclaving under standard conditions. The slant-grown organism was used to inoculate a yeast/malt extract medium and was grown for 7 days on a rotary shaker at 200 rpm, at room temperature. An inoculum from the liquid culture was regrown in yeast/malt extract medium under similar conditions.

The culture material was disrupted by blending at high speed in a blender at 4° C. to break up mycelial filaments into small fragments, and these were plated out on yeast-malt extract agar plates. The plated colonies were transferred to liquid-medium growth flasks, and grown up under standard conditions. The cells were disrupted, and the contents of the cells assayed for the ability to convert glucose to glucosone. Glucosone production was determined using the triphenyltetrazolium chloride assay, which gives a strong colorimetric reaction in the presence of glucosone (Mattson, et al., *Anal. Chem.* 22:182 (1950).

Those cells which were the highest producers of glucosone were then recultured according to the method used initially. The resulting *P. obtusus* culture was composed of a substantially uniform population of relatively high P2O producers, denoted herein as the T strain. *P obtusus* T strain cultures have been deposited by us at NRRL under No. 15594. They are also deposited at CMCC under No. 1421.

The cultured T strain was washed in buffer and disrupted by blending, as above. The disrupted culture material was added to a petri dish, in an amount just sufficient to cover the bottom of the dish, and irradiated with a General Electric 15W germicidal ultraviolet lamp for about 1-2 minute, while stirring the material rapidly with a magnetic stirrer to produce even irradiation of the cells. The irradiation time and flux density were varied, the flux density by varying the distance between lamp and dish, to produce a survival rate of about 1-5%, based on number of colonies observed by agar plating before and after irradiation. Following mutagenesis with UV light, the cells in the flask were plated out on yeast/malt extract agar plates, and the colonies formed on the plates were grown up in liquid medium and assayed, as above described for the T strain, for their ability to convert glucose to glucosone enzymatically in a broken-cell assay.

A culture of one mutagenized, high-producer strain selected from among the mutagenized cell material produced about five times as much P2O based on enzyme units per liter of culture material after six days, as that produced by the parental ATCC #26733 strain. Cultures of the high-producer strain, designated AU124, have been deposited at the NRRL, under No. 15595. Cultures of the strain are also deposited at CMCC under No. 1500.

EXAMPLE II

P2O enzyme preparation from *P. obtusus*

*P. obtusus*, strain AU124 was grown on yeast/malt extract agar slants at pH 6.4. The slant-grown culture was used to inoculate a yeast/malt extract medium and was grown for 8 days on a rotary shaker at 200 rpm at room temperature. The culture was vacuum filtered through number 541 Whatman Paper.

The mycelia obtained from 400 ml of culture were washed twice with 0.05M sodium phosphate buffer, pH 7.5, containing 10 mM EDTA and 50 $\mu$g/ml fresh phenylmethylsulfonyl fluoride (PMSF). The mycelia were homogenized for 2 minutes in a Waring blender with 70 ml of 0.05M sodium phosphate buffer pH 7.5, containing the above concentrations of protease inhibitors. The homogenate was centrifuged at 6,000 rpm for 20 minutes and the supernatant, containing the P2O activity, was decanted and placed in a 500 Erlenmeyer flask. Polyethylene glycol was added to a final concentration of 19 grams per 100 ml. The solution was stirred and then allowed to stand at 40 minutes at 4° C. The precipitate was recovered by centrifugation at 10,000 rpm for 20 minutes.

The supernatant from the centrifugation step was decanted and discarded, and the pellet, containing the P2O enzyme activity, was resuspended by vortexing in 30 ml of 0.025M sodium phosphate buffer pH 7.5, containing 0.1M sodium chloride and protease inhibitor(s) at the above-mentioned concentrations. The purification was carried out as rapidly as possible at 4° C. to minimize proteolysis of the P2O enzyme.

The suspension was allowed to stand for 30 minutes, during which time a precipitate formed, then centrifuged at 10,000 rpm for 20 minutes. The resulting clear, yellow supernatant had a specific activity of about 4 units per milligram of protein, as compared with about 0.5 units per milligram of protein in the supernatant fluid of the crude, cleared lysate. The enzyme so obtained is also referred to herein as a partially-purified P2O enzyme preparation.

The P2O enzyme preparation was tested for its ability to convert substantially pure glucose to glucosone at pH 6.0 in the presence of oxygen and catalase. The catalase used was a higher purified *A. niger* catalase obtained from Fermco, Inc. (Elk Grove, Illinois) (Lot No 4927, 154$\mu$/mg). Glucose-1-oxidase contaminants in the catalase were removed by purification using DEAE chromatography. One gram of catalase was purified by elution from a 5×12 cm column using a 0-150 mM NaCl gradient in 20 mM sodium acetate (pH 4.7). The bulk of the catalase activity eluted in a peak which was well separated from glucose-1-oxidase activity. Catalase was monitored by absorption of its heme group at 404 mM.

Conversion of a 2% glucose solution in 0.1M sodium phosphate, pH 6.0, to products was carried out in a total volume of 500 microliters in a 13×100 mm glass test tube. The reaction solution contained 0.46 units of the partially purified P2O enzyme preparation, and purified catalase. The tubes were shaken at 250 rpm at 25° C., 90% relative humidity, for 6 hours and the reaction terminated by freezing.

The samples, after thawing, were analyzed by HPLC, using a Waters microbondapack carbohydrate column (Waters Corp.; Milford, MA), monitored by refractive index and ultraviolet absorption at 192 mM. The results are shown in FIG. 3A. Glucosone was identified by its elution position compared with a known glucosone standard. As seen in FIG. 3A, the partially purified P2O preparation produces substantial quantities of one or more non-glucosone by-products.

EXAMPLE III

Purification and characterization of *P. obtusus* P20 O

The P2O enzyme preparation from Example II was purified further using DEAE chromatography in 30 mM TRIS-HCl, pH 8.5, containing 2 mM EDTA and 10 $\mu$g/ml PMSF. The sample was eluted from a 5×16 cm column using a gradient of 0-300 mM NaCl. P2O activity was monitored using the orthodianisidine colorometric assay for the proxide co-product, essentially as described by Ruelius et al., Biochim et Biophys. Acta 167, 493-500 (1968). P2O activity eluted at about 50 mM NaCl. Fractions containing the peak activity were pooled and concentrated to 0.5 ml by ultrafiltration using Amicon filters obtained from Amicon Corp. (Danvers, MA). Biogel P300 was obtained from Biorad Laboratories (Richmond, CA). The sample was further purified by molecular sieve chromatography using a 1.5×95 cm Biogel P300 column in 100 mM sodium phosphate, pH 7 buffer. The P2O activity eluted at a sharp peak corresponding to an apparent native molecular weight of about 290,000 daltons.

The purity of the P2O fraction which eluted from the P300 column was examined by sodium dodecyl sulfate polyacrylamide gel electrophoresis (SDS-PAGE), according to a standard procedure. The P2O sample showed a single band having a migration distance corresponding to a molecular weight of about 68,000 daltons. The enzyme was judged to be about 98% pure, based on the relative intensity of the faint contaminant protein bands with respect to the major band corresponding to P2O subunit.

The purified P2O enzyme had a specific activity of about 8.6 units per milligram, representing an approximately 22-fold purification over the activity of P2O seen in cleared lysates. The amount of enzyme recovered was about 40% of the total starting material.

The approximate 290,000 dalton molecular weight of the native P2O enzyme and its approximate 68,000 subunit molecular weight suggest that the protein is a homotetramer. The enzyme appears to contain one covalently bound flavin molecular per subunit (detectable as UV-fluorescence in the 68,000 dalton SDS-PAGE band), and has absorption maxima at 276, 357 and 456 nm. The enzyme has a sedimentation coefficient of about 11.4, as determined by sucrose gradient ultracentrifugation. The relative activities of the enzyme, on D-glucose, L-sorbose, D-xylose, and D-gluconolactone are 100:80:48:12, respectively, at about 1% (w/v) substrate concentration. As noted above with respect to FIG. 2, the enzyme has a broad pH optimum of between about 4.5 and 5.5.

EXAMPLE IV

Glucosone production with purified P2O

The purified P2O obtained in accordance with Example III was used to convert glucose to glucosone in a reaction substantially identical to that described in Example II. Briefly, 0.46 International Units of the enzyme were mixed in a 0.5 ml reaction medium containing 2% glucose in 0.1 M sodium phosphate, pH 6.0, and purified catalase. The reaction was performed at 25° C. in the presence of air, at 90% relative humidity, for 6 hours. The reaction products were analyzed by HPLC, with the material eluted being monitored by ultraviolet light absorption at 192 mm. The absorbance profile of the material produced in the reaction is shown in FIG. 3B. Here it is seen that substantially all of the material produced is in the prominent peak identified as glucosone, with very little by-product material being formed. A comparison of FIGS. 3B and 3A shows the importance of removing glucosone-utilizing enzyme contaminants, including primarily, if not solely, PD, in improving both the yield and purity of the glucosone produced by P20O.

EXAMPLE V

Heat-treating the P2O enzyme preparation

A P2O enzyme preparation was prepared from *P. obtusus* AU124 substantially in accordance with the method described in Example II. The P2O enzyme in the preparation was substantially unproteolyzed by virtue of the protease inhibitors used during the preparation steps. A second P2O enzyme preparation studied was prepared in substantially the same way, except that no protease inhibitor was used in any of the preparation steps. When the P2O of this preparation was purified substantially to homogeneity, it was found to have variable subunit molecular weights, principally molecular weights of about 65,000 daltons, 34,000 daltons, 30,000 daltons, and approximately 4,000 daltons, indicating partial proteolysis of the enzyme.

Heat-treatment of each enzyme preparation was carried out at pH 5.0 in 50 mM sodium citrate, 1 mM EDTA, at 65° C. The P2O activity in each preparation was measured at the beginning of the heat-treatment and after 15, 30, 60 and 90 minutes of heating at 65° C. P2O activity was determined at 25° C. by oxygen consumption in the presence of glucose, using an oxygen electrode according to known methods. In FIG. 1, it is seen that P2O, which is largely unproteolyzed, loses less than about 10% of its activity after incubation at 65° C. for 15 minutes, and about 20% of its original activity after 90 minutes of heat-treatment. By contrast, the partially proteolyzed P2O loses about 30% of its activity in the first 15 minutes and more than half of its activity after 90 minutes of heating.

PD was removed from the nonproteolyzed P2O enzyme fraction and purified substantially to homogeneity. Briefly, the PEG-precipitated *P. obtusus* P2O enzyme preparation was fractionated using DEAE chromatography, pH 8.5. The PD enzyme was identified by its ability to convert glucosone to products having optical absorption at 230 and 265 nm. To remove minor contaminants, the column fractions containing maximal PD activity were rechromatographed on a smaller DEAE column, using the same conditions. Peak enzyme fractions from the second DEAE column were further purified on a carboxymethyl sepharose column (Pharmacia CL-6B) and eluted therefrom, at pH 5.5, by a 0–200 mM NaCl gradient in 50 mM sodium acetate, pH 5.5. The resulting partially purified PD was diluted into 50 mM sodium acetate, pH 5.0, containing 1 mM EDTA and a small amount of purified *P. obtusus* P2O and heat-treated at 65° C. for time intervals ranging from 5 minutes to 30 minutes. When the enzyme solution was readjusted to pH 6.0 and reassayed at 22° C., the PD was found to have lost substantially all of its activity after 15 minutes of heating at 65° C. The P2O in the same solution retained substantially all of its activity after the same 15 minute treatment, similar to what is shown in FIG. 1.

EXAMPLE VI

Glucosone production using heat-treated P2O enzyme preparation

The partially proteolyzed P2O enzyme preparation from Example V was heat-treated, at pH 5.0, for 15 minutes at 65° C. The heat-treated fraction was reacted with 2% glucose under conditions identical to those described in Example II. The reaction products were separated by HPLC and monitored at 192 nm, with the results seen in FIG. 3C. It can be seen from a comparison of FIGS. 3C and 3A that heat-treating the P2O enzyme preparation produced a substantial increase in the yield of glucosone, and a corresponding decrease in by-products.

EXAMPLE VII

*P. obtusus* P2O and PD pH Profiles; Molecular Weight of PD

P2O and PD from *P. obtusus*, strain AU124, were isolated in accordance with the methods described in Examples III and V, respectively. The activity of the P2O enzyme, as determined by the rate of $O_2$ consumption in the presence of glucose, was measured over a pH range from about 3.0 to 7.0. The pH profile of P2O, indicated by the dashed line in FIG. 2, shows that the enzyme pH optimum is between 4.5 and 5.5. Similarly, the pH profile of the purified PD, as determined by its ability to convert glucosone to the product which absorbs at 265 nm, was measured over a pH range from about 4.0 to 10.0. The PD pH profile, indicated in solid lines in FIG. 2, shows that the enzyme has a pH optimum of about 7.5, and displays less than about 5% of its optimal activity when assayed at pH 4.4.

PD-containing fractions with peak activity eluted from the carboxymethyl sepharose column as described in Example V, were pooled and concentrated to 0.5 ml, using Amicon PM30 ultra-filtration, and then sized according to native molecular weight by molecular sieve chromatography using a 1.5×95 cm Biogel P300 column, with 100 mM sodium phosphate buffer, pH 7.0. PD activity eluted as a sharp peak at an apparent native molecular weight of about 200,000 daltons. Using peak and side fractions from the Biogel P300 sized column, PD was further analyzed by SDS-PAGE according to a standard procedure. The sample showed a single band with molecular weight of about 98,000 daltons. PD from *P. obtusus* is thus apparently composed of two identical subunits.

EXAMPLE VIII

Glucosone production with the P2O enzyme preparation at pH 4.4

The enzymatic conversion of glucose to glucosone by the partially purified P2O enzyme preparation from Example II at pH 4.4 was studied. The reaction conditions were substantially identical to those described in Example II, except that the reaction was carried out at pH 4.4, using a 0.1 M sodium citrate buffer rather than the 0.1 M sodium phosphate buffer used for the pH 6.0 reactions described in Examples II, IV and VI. The reaction products were analyzed by HPLC, and monitored at 192 nm, with the results shown in FIG. 3D. The pH remained substantially unchanged over the 6 hour reaction period. As seen from the absorbance profile in FIG. 3D, performing the reaction at pH 4.4 leads to a very high yield and purity of glucosone, and almost complete suppression of by-products formed in the reaction.

It was seen in Example VII above that the PD enzyme contained in the *P. obtusus* P2O enzyme preparation is largely inactive at pH 4.4. The fact that by-product formation is largely suppressed at pH 4.4 indicates that (1) PD is the major, if not sole, glucosone-utilizing enzyme contaminant in the P2O enzyme preparation and/or (2) the PD pH profile, and particularly its low activity at pH below about 4.4, is typical of other glucosone-utilizing enzyme contaminants in the P2O preparation.

EXAMPLE IX

Glucosone production with purified P2O at pH 4.4

The present example demonstrates the high product yield and purity achievable in a glucose-to-glucosone reaction using a substantially purified P2O enzyme and carrying out the reaction at pH 4.4. The reaction conditions used were substantially those used in Example VIII, except that P2O enzyme derived from *P. obtusus* AU124 and purified in accordance with Example III was used instead of the partially purified P2O enzyme preparation from Example II. The products were analyzed by HPLC, as monitored at 192 nm, with the results shown in FIG. 3E. The results indicate that substantially no by-products were formed during the 6 hour reaction period. The purity of glucosone produced in the reaction was estimated to be greater than 99%, based on the relative peak areas of glucosone and byproducts.

EXAMPLE X

Selection of P2O-producing microorganism lacking PD enzyme activity

This example illustrates another embodiment of the method of the invention for providing a P2O enzyme which is substantially free of pyranosone-utilizing enzyme contaminants at a selected pH between about 4.4 and 6.5.

A number of fungal species have been found to be capable of converting glucose to glucosone. These include *Aspergillus flavus* (C. Berkeley, Biochem. J. 27, 1357 (1933); *Aspergillus parasiticus* (C. Berkeley, Biochem. J. 31, 1033 (1937); *Polyporus obtusus* (Janssen and Ruelius (1968), supra); *Corticium caeruleum* (Baute, et al. (1977), supra); and *Oudemansiella mucida* (Volc, et al., Coll Czech. Chem. Commun. 45, 950 (1980). The ability of a microorganism to convert glucose to glucosone presumably requires that the microorganism possess an enzyme or enzyme system with glucose-2-oxidase activity. The *P. obtusus* and *O. mucida* species have been shown to have an enzyme or enzyme system with pyranose-2-oxidase activity. Janssen and Ruelius (1968), supra; Volc, et al. (1980), supra. Both of these species are white-rotting fungi ("white-rotters") of the Basidiomycete family. Only in the case of *P. obtusus* has a partially pure pyranose-2-oxidase or glucose-2-oxidase enzyme preparation, substantially free of cell material, been obtained. Janssen and Ruelius (1968), supra.

Glucose-2-oxidase activity, and by implication pyranose-2-oxidase activity, are not found in all fungal species, even in all white-rotting fungal species, and apparently not even in all species of any fungal genus which has at least one species which has glucose- or pyranose-2-oxidase activity.

163 fungal strains, including the following 13 white-rotters:

(1) *Laetiporus sulfureus* M-4
(2) *Laetiporus sulfureus* F-4
(3) *Phellinus gilvus*
(4) *Ganoderma applanatum*
(5) *Phellinus pini*
(6) *Pleurotus ostreatus*
(7) *Poria andersonii*
(8) *Stereum sp.*
(9) *Coriolus versicolor*
(10) *Ganoderma lucidum*
(11) *Lenzites betulinus*
(12) *Armillariella mellea*
(13) *Stereum hirssutum* were screened as follows for glucose-2-oxidase activity. The strains were obtained from various sources, including nature and depositories such as ATCC and NRRL. *P. obtusus* and *O. mucida* strains were not included. All strains were obtained and stored as slant cultures. The 13 white-rotting strains were provided by Prof. Sara Fultz of Stanford University, Palo Alto, California from her culture collection.

A culture of each of the 163 strains was grown on approximately 3 ml of F4 agar, and another culture of each of the strains was grown on approximately 3 ml of FA agar. F4 agar consists of 5.0 g tryptone, 3.0 g malt extract, 10.0 g glucose, 3.0 g yeast extract and 0.2 g agar combined with 1.0 l of distilled water (See Pansey, et al. Antimicrob. Agents Chemotherapy, 399 (1966). FA agar is prepared by combining 15.0 g glucose, 3.0 g yeast extract, 1 ml artificial sea water (from Aquarium systems Inc., Eastlake, Ohio) and 0.2 g agar with 966 ml of distilled water (See V. Lilly and H. Barnett, *Physiology of the Fungi*, McGraw-Hill Book Co., Inc., New York, NY (1951)), then autoclaving the mixture for 15 minutes at 15 psi pressure, and finally adding 100 micrograms thiamine and 5 microgram biotin via filter sterilization. Cultures on both of the agars were grown and assayed in the same manner, as follows.

A culture was inoculated into the approximately 3 ml of agar, in a capped sterile vial, by picking the slant culture on which the strain was received and stored, with a sterilized toothpick and then aseptically touching the tip of the toothpick to the surface of the agar pad approximately at its center. Growth was continued for 2 to 4 days at 25° C., as long as required for the organism to cover the agar pad. All of the above-listed 13 white-rotter strains were grown for 4 days.

After the 1–4 day growth period, 5.0 ml of sterile 2% (w/v) glucose solution, buffered to pH 6.0 with 35 mM potassium phosphate buffer, was introduced asceptically into the vial; and the vial was then shaken at 250 rpm for 24 hours at 25° C.

After the shaking, 1.0 ml of fluid was removed from the vial and immediately processed for testing for the presence of glucosone. The first step in the processing was to add to the 1.0 ml of fluid 0.2 ml of a solution of 2% (w/v) 2,4-dinitrophenylhydrazine in 30% perchloric acid. This solution was then analyzed by thin-layer chromatography (TLC) for the presence of the bis-2,4-dinitrophenylhydrazone of glucosone. The TLC carried out with a Selectasol ® system from Schleicher and Schuell (Keene, New Hampshire) using 0.25 mm silica gel plates, 25% (v/v) xylene in ethyl acetate (a solution in which the bis-2,4-dinitrophenylhydrazone of glucosone is soluble and into which it can be extracted from aqueous solution) as carrier, and a spray of 20% (v/v) 4.8 M NaOH (in water) with ethanol to develop the plates. The bis-2,4-dinitrophenylhydrazone of glucosone is purple on the developed plates.

The TLC assay could detect glucosone from a culture if as little as 0.08% of the glucose in the culture system (after addition of the 2% glucose solution just prior to the 24-hour shaking) was present as glucosone at the time the 2,4-dinitrophenylhydrazine was added to the 1.0 ml of culture removed for assay. A finding of detectable glucosone in the assay of a culture indicted the fungal strain in the culture had a glucose-2-oxidase activity of potential commercial valve.

The same assay technique could have been used with xylose instead of glucose to detect xylose-2-oxidase activity via the formation of the hydrazone of xylosone.

Of the 163 strains screened, only 2 were found to possess glucose-2-oxidase activity, both of which produced glucosone when cultured on either F4 or FA agar. The remaining 161 strains produced no detectable glucosone when grown on either agar.

Both producing strains are from the 13 white-rotters listed above: *Coriolus versicolor*, now deposited in the CMCC under No. 0748 and in the NRRL under No. 15152, and *Lenzites betulinus*, now deposited in the CMCC under No. 0749 and in the NRRL under No. 15593.

A culture of *C. versicolor*, deposited by us at NRRL, under No. 15152, and at CMCC under No. 0748, was grown out under culture conditions similar to those used to culture *P. obtusus*, ATCC 26733, as detailed in Example I above. The cultured cells were plated on agar plates and selected for high producers of P2O, substantially as described in Example I, leading to cultures of substantially uniform, relatively high producers. The best culture found produced P2O at a yield, expressed in International Units per liter of growth medium, after 6 days of incubation, which was approximately 30% that produced by the above-identified *P. obtusus* strain AU124.

This best culture of *C. versicolor* was assayed for PD activity by its ability to convert glucosone to a product having an absorption peak at 265 nm. No PD activity was detected under a variety of assay conditions at a variety of pH's.

A culture of *L. betulinus*, deposited at NRRL under No. 15593 and at CMCC under No. 0749, was grown under conditions similar to those used to culture *P. obtusus*, ATCC 26733, as described in Example I. The *L. betulinus* culture was found to contain a 2 to 3-fold variability in the amount of P2O produced by cultures grown from individual cells, plated out from this initial culture, similar to what was observed for cultures derived from cultured cells of *P. obtusus*, ATCC 26733, and *C. versicolor* NRRL 15152. Cells from the *L. betulinus* culture were plated on agar, and selected for high producers of P2O, substantially as described in Example I, leading to cultures of substantially uniformly high producers. The best culture found produced P2O at a yield, based on enzyme activity units per liter of growth medium, approximately 70% of that of the best culture of *C. versicolor* described above.

This best culture of *L. betulinus*, was assayed for PD activity as just described, like *C. versicolor*. The results showed that *L. betulinus* also produces substantially no detectable soluble PD.

EXAMPLE XI

Preparation and Characterization of *C. versicolor* P2O

The high-producer culture of *C. versicolor* described in Example X was grown in submerged culture in 1.5 liters of yeast/malt extract medium at 28° C. for 7 days. The resulting mycelial balls were collected by filtration, washed, and then disrupted at 4° C. in 50 mM sodium phosphate, pH 7.0, for 3 minutes using an Ultraturrax blender. The lysate was cleared by centrifugation 25 minutes at 12,000 rpm. To concentrate and partially purify the enzyme, solid ammonium sulfate was slowly added to 55% saturation, and the solution was allowed to stand for 90 minutes at 4° C., prior to collecting the precipitate. The precipitate was resuspended in 42 ml of 30 mM TRIS-HCl, pH 8.5, dialyzed against the same buffer, and centrifuged at 10,000 rpm for 15 minutes to remove a precipitate.

The enzyme was applied to a 2.6×40 cm DEAE column, washed, and eluted using a 0–300 mM NaCl gradient. The P2O elutes at about 220 mM. Portions of each fraction were assayed for P2O activity, by monitoring peroxide generation conventionally. Protein concentration was also determined by a conventional method. The fractions containing P2O activity were pooled and concentrated by ultrafiltration with an Amicon PM10 filter obtained from Amicon Corp. Peak fractions were dialyzed into 30 mM sodium acetate (pH 5.5), adjusted to 1.5 M NaCl and loaded onto a phenyl-sepharose column. The P2O was eluted with a 0–1.5 M NaCl gradient in 50 mM sodium acetate, pH 5.5. The enzyme eluted at about 1.1 M NaCl. Fractions containing the peak activity were pooled and concentrated to 0.5 ml by Amicon PM30 ultrafiltration and sized according to native molecular weight using a 1.5×95 cm Biogel P300 column. Elution was at 0.1 ml/minute with 100 mM sodium phosphate, pH 7.0. Using known molecular weight markers in the column, the enzyme's apparent native molecular weight was calculated to be about 130,000 daltons. A single band having a molecular weight of about 65,000 was observed when the enzyme was analyzed by SDS-PAGE. The enzyme thus appears to be a homodimer. The enzyme was judged to be about 95% pure, based on the staining intensity of protein bands in SDS-PAGE.

Cofactor analysis indicated that each subunit of the enzyme contains a flavin moiety which appears to be covalently attached. The protein has absorption maxima at 276, 357 and 454 nm.

The relative activities of the enzyme on the substrates D-glucose, L-sorbose, D-xylose and delta-D-gluconolactone are 100: 74: 41: 6, respectively, at 1% (w/v) substrate concentration. The enzyme has a pH optimum of about 5.0.

EXAMPLE XII

Preparation and characterization of P2O from *L. betulinus*

The high-producer culture of *L. betulinus* described in Example X was grown according to the conditions described in Example II. The cells were homogenized and centrifuged to produce a supernatant, also in accordance with the methods described in Example II. Polyethylene glycol was added to the supernatant to a final concentration of 20%, and the mixture was allowed to stand for 2 hours at 4° C., producing a precipitate which was pelleted by centrifugation.

The resulting clear yellow supernatant was further purified using DEAE chromatography in 30 mM TRIS-HCl, pH 8.5, and eluted from the 5×16 cm column using a 0–300 mM NaCl gradient. The protein eluted at about 75 mM NaCl. Fractions containing the peak of P2O activity were pooled and concentrated to 0.5 ml by Amicon PM30 ultrafiltration, and then fractionated, according to native molecular weight, using a 1.5×95 cm Biogel P300 column. The column was run at a flow rate of 0.1 ml per minute, using 100 mM sodium phosphate, pH 7.0. The protein eluted in a fraction corresponding to an apparent native molecular weight of about 300,000 daltons. Analysis of the purified protein by SDS-PAGE showed one major band corresponding to a molecular weight of about 65,000 daltons, and minor bands, presumably representing impurities. Based on the molecular weight data, the protein appears to be a homotetramer.

The enzyme contains a covalently attached flavin on each subunit, and has absorption maxima at 275, 360, and 450 nm. The relative activities of the purified enzyme on the pyranose substrates D-glucose, L-sorbose, D-xylose and delta-D-gluconolactone are 100: 43: 43: 26, respectively, at 20 mM substrate concentration. The enzyme has a broad pH optimum between about 5 and 6.

EXAMPLE XIII

Effect of $H_2O_2$ on P2O half-life.

A P2O enzyme preparation was derived from *P. obtusus* AU124 in accordance with the method detailed in Example II. *A. niger* catalase was obtained from Fermco, Inc., and further purified by DEAE ion-exchange chromatography to remove glucose-1-oxidase activity present in the commercially available enzyme, as in Example II. A phenol-formaldehyde bead support, ES-762, was obtained from Diamond Shamrock (Foster City, CA).

Reagents containing the various activity ratios of P2O to catalase shown in Table I were prepared by sequential adsorption of first catalase and then P2O to the support. The activity ratios of P2O to catalase in the four supports is the theoretical steady-state level of $H_2O_2$ in moles per liter expected in a P2O-reaction, assuming no inactivation of either enzyme.

TABLE I

| Reagent | P2O/Catalase (activity ratio in M) | [$H_2O_2$] (mM) | P2O Half Life (Normalized) |
|---|---|---|---|
| #1 | no catalase | 10 | 1 |
| #2 | $0.67 \times 10^{-3}$ | 2.0 | 8.0 |
| #3 | $0.45 \times 10^{-3}$ | 0.3 | 11.6 |
| #4 | $0.07 \times 10^{-3}$ | 0.04 | 28–60 |

Each of the supports was packed in a 7 mm×1.2 M glass Pyrex column reactor by pouring a slurry of the support over about 10 inches of 1 mm diameter non-porous glass beads, and applying a low vacuum to the bottom to aid in settling the bed. When a packed column height of 25 inches was reached, another 10 inches of glass beads were placed on the resin bed followed by approximately an inch of glass wool. After circulating sterile water through the bed to wash out any excess reagents or colored material, the column was equilibrated with 25 mM citrate, pH 5.5.

The reaction was started up by introducing a 5% solution of glucose in citrate buffer through the column. The level of $H_2O_2$ which eluted from the reactor column was monitored over a period of continuous column operation of about 12 days.

The reactor packed with reagent #1, containing only P2O, showed an immediate burst of $H_2O_2$, to approximately 100 mM, followed by a steady decline in $H_2O_2$ concentration to about 10 mM by the third day of continuous operation.

The reactor packed with reagent #2 showed a steady increase in $H_2O_2$ concentration from a level of about 0.3 to 3 mM, over the first four to five days of reactor operation, indicating a slow inactivation of catalase, presumably by the $H_2O_2$ being produced in the P2O reaction. From the maximum concentration of about 3 mM, the $H_2O_2$ concentration declined gradually to about 0.3 mM by the twelfth day of reactor operation.

For both reagents #3 and #4, the reactor $H_2O_2$ concentration started from initial levels at or below about 0.3 mM, and remained substantially constant over a several day reaction period, and then showed increases of up to about 0.7 mM and 0.3 mM, respectively, by the twelfth day of the reaction. The increase in $H_2O_2$ concentration suggests greater $H_2O_2$ inactivation of catalase than P2O. The $H_2O_2$ concentrations in the four reactors, measured after three days of column operation, are listed in the third column in Table I. The measured concentrations of $H_2O_2$ are consistent with the theoretical $H_2O_2$ concentrations calculated from the associated P2O to catalase activity ratios.

For each of the four reagents, the half-life of the P2O enzyme was determined by monitoring the rate of glucosone production in the corresponding reaction during the 12-day course of the reaction. Glucosone levels produced by each reactor were measured using the above-described triphenytetrazolium colorometric assay for glucosone. The half-life data are shown at the right-hand column in Table I. The actual half-life values have been normalized to an arbitrary unit value of 1 for the reagent #1 lacking catalase. The data show that the half-life of P2O is increased about 11-fold by employing a P2O to catalase ratio which maintains the $H_2O_2$ concentration below about $3 \times 10^{-4}$ M (reagent #3) and can be increased between about 28 and 60 fold by employing a P2O to catalase activity ratio which maintains the $H_2O_2$ concentration in the reactor below about $4 \times 10^{-5}$ M.

EXAMPLE XIV

Production of substantially pure glucosone

A P2O enzyme preparation obtained from *P. obtusus*, strain AU124, was prepared in accordance with Example II, and the P2O enzyme was purified substantially to homogeneity in accordance with Example III. The enzyme was used to convert glucose to glucosone under the following conditions: The purified P2O (0.46 units) and catalase were added to 500 microliters of unbuffered medium, pH 5.0. Glucose was added to a final concentration of about 5%. The reaction was carried out at room temperature, under 90% relative humidity, until all of the glucose substrate was consumed. The pH of the solution remained constant at 5.0 throughout the reaction period without the addition of a base to the reaction mixture.

At the end of the reaction period, the reaction products were analyzed by HPLC, monitored at 192 nm, as described in Example IV. The absorption profile of the HPLC-fractionated products is shown in FIG. 5. Here it is seen that the reaction produces substantially pure glucosone. The glucosone was judged to be greater than 99% pure, based on the relative areas of the peaks associated with glucosone and reaction by-products.

The results of this study illustrate that where glucosone breakdown is prevented, according to the method of the invention, the pH of the reaction medium is substantially stable, thereby eliminating the need to control reaction pH with a strong buffer and/or by the periodic addition of base to the reaction.

While preferred embodiments of the invention have been described with reference to the examples herein, it will be appreciated that various changes and modifications can be made without departing from the spirit and scope of the invention.

What is claimed is:

1. A substantially pure pyranose-2-oxidase preparation, which is substantially free of glucosone-utilizing enzyme contaminants including pyranosone dehydratase activity which have measurable activity at a pH between about 4.4 and 7.0, prepared from mycelia of a *C. versicolor* culture.

2. A substantially pure pyranose-2-oxidase preparation, which is substantially free of glucosone-utilizing enzyme contaminants including pyranosone dehydratase activity which have measurable activity at a pH between about 4.4 and 7.0, prepared from mycelia of an *L. betulinus* culture.

3. The preparation of claim 1 having pyranose-2-oxidase characteristics of
   a dimeric molecular weight of about 130,000 daltons,
   a subunit molecular weight of about 65,000 daltons,
   covalently bound flavin,
   absorption maxima at 276, 357, and 454 nm,
   relative activities toward the substrates glucose, sorbose, xylose and delta-gluconolactone of about 100: 74: 41: 6: respectively, at 1% (w/v) substrate concentrations, and
   a pH optimum of about 5.0.

4. The preparation of claim 1, wherein the culture of *C. versicolor* cells has the characteristics of the culture of *C. versicolor* cells deposited at NRRL under No. 15152.

5. The preparation of claim 2, having pyranose-2-oxidase characteristics of
   a tetrameric molecular weight of around 300,000 daltons,
   a subunit molecular weight of about 67,000 daltons,
   covalently bound flavin,
   absorption maxima at 275, 360, and 450 nm,
   relative activities toward the substrates glucose, sorbose, xylose and delta-gluconolactone of 100: 43: 43: 26, respectively at 20 mM substrate concentrations, and
   a pH optimum of about 5.5.

6. The preparation of claim 2, wherein the culture of *L. betulinus* cells has the characteristics of the culture of *L. betulinus* cells deposited at NRRL under No. 15593.

* * * * *